(12) United States Patent
Gross et al.

(10) Patent No.: US 9,618,515 B2
(45) Date of Patent: Apr. 11, 2017

(54) ASSAY TO CAPTURE AND DETECT CIRCULATING MULTIPLE MYELOMA CELLS FROM BLOOD

(75) Inventors: Steven Gross, Ambler, PA (US); Mark Carle Connelly, Doylestown, PA (US); Galla Chandra Rao, Princeton Jct., NJ (US); Marielena Mata, Philadelphia, PA (US); Carrie Morano, Hamilton, NJ (US)

(73) Assignee: Janssen Diagnostics, LLC, Raritan, NJ (US)

(*) Notice: Subject to any disclaimer, the term of this patent is extended or adjusted under 35 U.S.C. 154(b) by 701 days.

(21) Appl. No.: 13/554,623

(22) Filed: Jul. 20, 2012

(65) Prior Publication Data

US 2013/0189675 A1 Jul. 25, 2013

Related U.S. Application Data

(60) Provisional application No. 61/510,170, filed on Jul. 21, 2011.

(51) Int. Cl.
| | | |
|---|---|---|
| G01N 33/551 | (2006.01) | |
| G01N 33/566 | (2006.01) | |
| G01N 33/574 | (2006.01) | |
| B03C 1/01 | (2006.01) | |
| B03C 1/28 | (2006.01) | |

(52) U.S. Cl.
CPC ......... *G01N 33/57492* (2013.01); *B03C 1/01* (2013.01); *B03C 1/28* (2013.01); *G01N 33/57426* (2013.01); *B03C 2201/26* (2013.01)

(58) Field of Classification Search
None
See application file for complete search history.

(56) References Cited

U.S. PATENT DOCUMENTS

| | | | |
|---|---|---|---|
| 5,597,531 A | | 1/1997 | Liberti et al. |
| 5,646,001 A | * | 7/1997 | Terstappen ............... A23L 3/32 209/213 |
| 5,698,271 A | | 12/1997 | Liberti et al. |
| 5,840,502 A | | 11/1998 | Van Vlasselaer |
| 6,365,662 B1 | | 4/2002 | Sakai et al. |
| 6,620,627 B1 | * | 9/2003 | Liberti ............ G01N 33/54326 422/533 |
| 7,011,794 B2 | | 3/2006 | Kagan et al. |
| 7,901,950 B2 | | 3/2011 | Connelly et al. |
| 2005/0181463 A1 | * | 8/2005 | Rao ............... G01N 33/54326 435/7.23 |

FOREIGN PATENT DOCUMENTS

| | | |
|---|---|---|
| CN | 101558309 A | 10/2009 |
| CN | 101600966 A | 12/2009 |
| CN | 101878429 A | 11/2010 |
| JP | 2005512557 | 7/2003 |
| WO | WO 99/41613 A | 8/1999 |
| WO | WO 2008/029290 A | 3/2008 |
| WO | WO 2008/031064 A | 3/2008 |

OTHER PUBLICATIONS

Rawstron et al (Haematologica, 2008, vol. 93, pp. 431-438).*
Grutzkau and Radbruch (Cytometry, Part A, 2010, vol. 77A, pp. 643-647, published on-line on May 20, 2010).*
Rawston et al (British Journal of Haematology, 1997, vol. 97, pp. 46-55).*
Matsui et al (Blood, 2004, vol. 103, pp. 2332-2336).*
Witzig et al, "T cell depletion using anti-CD2 coated magnetic beads simplifies the detection of peripheral blood plasma cells" Journal of Immunological Methods, Elsevier Science Publishers B.V.,Amsterdam, NL, vol. 144, No. 2, Nov. 22, 1991 (Nov. 22, 1991), pp. 253-256, XP023992217,DOI: 10.1 016/0022-1759(91 )90093-U.
Guillerm G et al: P16INK4A and P15INK4B Genes Methylation in CD138 Selected Plasms Cell from Monoclonal Gammopathy of Undetermined Significance Hematology Blood, American Society of Hematology, US, vol. 96, No. 11, Part 01, p. 471A Nov. 16, 2000 (Nov. 16, 2000), p. 471 A, XP00901 0439.
Bataille et al: Haematologica, Jan. 1, 2006 (Jan. 1, 2006),pp. 1234-1240, XP055255938, Retrieved from the Internet: URL:http://citeseerx.ist.psu.edu/viewdoc/download?doi=1 0.1.1.321.5570 &rep=rep1 &type=pdf.
CD138 expression on circulating myeloma cells: disease activity correlation, Haematology Oct. 16, 2009 (Oct. 16, 2009), XP055255880, Retrieved from the Internet: URL:https://www.ibms.org/includes/act_download.php?download=pdf/Nov09-CD138.pdf.
Kumar S et al: Best Practice & Research Clinical Haematology, vol. 23, No. 3, Sep. 1, 2010 (Sep. 1, 2010), pp. 433-451, XP027521905,1SSN: 1521-6926.
Avet-Loiseau, et al. ""Genetic Abnormalities and Survival in Multiple Myeloma: The Experience of the InterGroupe Francophone du Myelome"" Blood, Apr. 15, 2007; 109: 3489-3495.
Kara et al: , Jul. 25, 2004 vol. 25 (11) (Jul. 25, 2004), XP055255966, Retrieved from the Internet: URL:http://smj.org.sa/index.php/smj/article/viewFile/5035/2809.
"Immunophenotype Characteristics in Multiple Myeloma Cells and Their Significance", Sun Ying et al., Journal of Experimental Hematology, vol. 18, No. 2, pp. 381-384; Paper 2. "Study on determining surface antigens in multiple myeloma cells with flow cytometry".
"Study on determining surface antigens in multiple myeloma cells with flow cytometry", Huang Chunni et al., Guangxi Medicine, vol. 29, No. 7, pp. 953-956, Jul. 31, 2007.
"Significance of CD138/Syndecan-1 for Multiple Myeloma Immunophenotypes", Zhuang Junling et al., Journal of Experimental Hematology, vol. 13, No. 6, pp. 1023-1027.
"The bone marrow pathology of multiple myeloma and diagnostic significance of immunohistochemical staining of CD38, CD138 antibodies", Zhang Xuemei et al., Clinical Focus, vol. 25, No. 10, pp. 892-893, May 20, 2010.

* cited by examiner

*Primary Examiner* — Karen Canella (57) ABSTRACT

The invention includes methods for isolating circulating multiple myeloma cells as well as method of treating patients suspected of having diseases of abnormal plasma cells.

2 Claims, 11 Drawing Sheets

Figure 1: CD138 Staining on Cell Lines H929, MM.1S and RPMI 8226

Figure 2: CD38 FITC and PE Staining on Cell Lines RPMI 8226, H929, and MM.1S

Figure 3: CD19 APC Staining on PBMC

Figure 4: CD19 APC Staining of PBMN at Various Dilutions

Figure 5: CD56 FITC Staining on PBMC

Figure 6: CD56 FITC Staining on Cell Lines

Figure 7    CD56 FITC Staining of H929 Cells at Various Dilutions

No CD56 FITC

Figure 8

1:5 Dilution of CD56 FITC

Figure 9

1:4 Dilution of CD56 FITC

Figure 10

1:3 Dilution of CD56 FITC

Figure 11: CellTracks® Images of Cell Lines H929 and MM.1S Recovered from CellSave Blood MM.1S Cells

Figure 12

H929 cells

Figure 13: CellTracks® Images of Carry-Over White Blood Cells from CellSave Blood Figure 14: CellTracks® Images of Multiple Myeloma Patient Samples Sample Number: 7

Figure 15

Sample Number: 8

Figure 16:

Sample Number: 4

Figure 17

Sample Number: 6

Figure 18: CellTracks® Images (Arrows) of CD38+, CD45/19- Cells from Normals

ASSAY TO CAPTURE AND DETECT CIRCULATING MULTIPLE MYELOMA CELLS FROM BLOOD

RELATED APPLICATIONS

This non-provisional filing claims priority to a provisional patent application, U.S. Patent Application Ser. No. 61/510,170, filed on Jul. 21, 2011.

BACKGROUND OF THE INVENTION

Multiple Myeloma (also known as myeloma or plasma cell myeloma) is a progressive hematologic cancer of the plasma cell. The condition is characterized by excessive numbers of plasma cells in the bone marrow and overproduction of intact monoclonal immunoglobulin or free monoclonal light chains.

Clinically the disease is diagnosed, staged, and treated based on a variety of parameters which include the myeloma tumor cell mass on the basis of the amount of monoclonal (or myeloma) protein (M protein) in the serum and/or urine, along with hemoglobin and serum calcium concentrations, the number of lytic bone lesions based on a skeletal survey, and the presence or absence of renal failure. Additional approaches to characterizing the condition include the detection of greater than ten percent (10%) of plasma cells on a bone marrow examination, the presence of soft tissue plasmacytomas and the detection of free kappa and lambda serum immunoglobulin light chain. Bone marrow examination is done using standard histology and immunohistochemistry techniques. Additional cytogenetics of bone marrow samples may be conducted to determine prognosis. Follow up surveillance consists of chemistry and bone marrow evaluations if clinically indicated due to its invasive nature.

Currently, flow cytometric analysis of bone marrow is being evaluated as a tool for disease characterization and to distinguish between neoplastic plasma cell disorders from normal plasma cells and to detect minimal residual disease. Nonetheless, this approach continues to rely on an invasive procedure. There is significant need to develop less invasive techniques to detect, monitor and characterize the disease throughout its history and the presence of these cells in the blood may provide that opportunity.

In addition, more sensitive tools need to be developed for more accurate assessment of risk and monitoring for progression of disease in earlier stages of disease including monoclonal gammopathy of undetermined significance (MGUS) and Smoldering Multiple Myeloma. Some research data suggest that circulating plasma cells can be detected in earlier stages of disease and may correlate with prognosis, supporting the use of a standardized methodology to capture, enumerate and characterize these cells in earlier stages of disease.

The general consensus within the literature (Report of the European Myeloma Network on Multiparametric Flow Cytometry in Multiple Myeloma and Related Disorders. Andy C. Rawstron et al. Haematologica, 2008; 93 (3).) for the identification of abnormal plasma cells, particularly by flow cytometry, has included several key biomarkers consisting primarily of CD138, CD38 and CD45. Additional biomarkers such as CD19 and CD56 have also demonstrated utility in diagnosis.

The instant invention investigates circulating myeloma cells to evaluate whether these particular biomarkers either alone or in combination with one or more additional biomarkers or with FISH can be used for both the capture and detection of abnormal circulating plasma cells including detection of minimal residual disease. FISH can be used to detect numerous cytogenetic abnormalities that have been described in multiple myeloma. Translocations at the IGH locus, t(4;14), and deletions at the p53 locus, del(17p), have been shown to have prognostic value for event free and overall survival in multiple myeloma. (Genetic Abnormalities and Survival in Multiple Myeloma: The Experience of the InterGroupe Francophone du Myelome. Nerve Avet-Loiseau et al. Blood, 2007; 109: 3489-3495) These probes and several other multiple myeloma markers are available in the Poseidon catalog and could be adapted for use with the CellTracks® platform.

Commercially there exist immunomagnetic selection kits using CD138 magnetic particles. Stem Cell Technologies has an EasySep® Human CD138 Positive Selection Kit which can select CD138 positive cells from bone marrow and peripheral blood mononuclear cells (PBMC) and Miltenyi Biotech has CD138 Microbeads for the selection of CD138 positive cells from bone marrow, PBMC and whole blood. Analysis of collected samples is typically performed using flow cytometry.

SUMMARY OF INVENTION

The invention described here consists of a method for the capture and detection of circulating plasma cells (CPC) and abnormal plasma cells or Multiple Myeloma cells ("CMMC") including the detection of minimal residual disease from peripheral blood. The instant invention provides a non-invasive means of detecting very low numbers of CMMCs in milliliter volumes of blood sample to detect, monitor and characterize the disease throughout its history, as well as provides the more sensitive tools for more accurate assessment of risk, and monitoring for progression of disease in earlier stages of disease including detecting circulating plasma cells in earlier stages of disease including monoclonal gammopathy of undetermined significance (MGUS) and Smoldering Multiple Myeloma. The capture and characterization of these circulating plasma cells from peripheral blood may provide novel biomarkers for the management of Multiple Myeloma patients.

Blood is collected in CellSave tubes which contains a preservative allowing for blood transport and storage while minimizing cell degradation. Cells are captured using colloidal magnetic particles conjugated to Syndecan-1 or CD138, a cell surface marker present on plasma cells. Once captured the cells are labeled with the additional cell markers CD38-PE (Phycoerythrin), CD19 and CD45-APC (allophycocyanin), and CD56-FITC (fluorescein isothiocyanate) in order to differentiate the Multiple Myeloma cells from background contaminating leukocytes (white blood cells). The ferrofluid and cell marker reagents are all part of a new CellSearch® CMMC service kit. The kit consists of 7 components of which 4 are identical to the reagents found in the Cellsearch® Epithelial Cell kit. These 4 common reagents are Capture Enhancement Reagent, Perm Reagent, Nucleic Acid Dye, and CellFix. The 3 new reagents consist of the CD138 Ferrofluid, a Staining Reagent consisting of CD38-PE, CD19 and CD45-APC and a separate marker staining reagent consisting of CD56-FITC.

DETAILED DESCRIPTION OF THE INVENTION

The invention includes a method of capturing, isolating and analyzing circulating multiple myeloma cells comprising (a) obtaining a sample of blood from a test subject (b) contacting said sample with colloidal magnetic particles that are conjugated to a first ligand (c) subjecting the sample of step (b) to a magnetic field to produce a separated fraction of magnetic particle-bound circulating multiple myeloma cells (d) treating the sample of step (c) with a first additional marker (e) analyzing circulating multiple myeloma cells.

As used herein the term "sample" refers to an amount of blood, preferably expressed as a volumetric measurement. The preferred volume of a blood sample is about 2 mL to 10 mL, more preferably 3-7.5 mL, most preferably 4 mL. The term "colloidal magnetic particles" refers to particles that are metallic or organometallic. Examples of such particles are disclosed in U.S. Pat. Nos. 5,597,531; 5,698,271; 5,698,271; 6,365,662, which are hereby incorporated by reference in its entirety, particularly for its description of such colloidal magnetic particles. They may be optionally coated with a polymer, preferably a polymer of biological origin such as bovine serum albumin and casein The term "ligand" refers to proteins that bind to cell associated markers of CMMCs or of circulating plasma cells ("CPC"s). The preferred proteins are antibodies, preferably anti CD 138, anti-CD 38, and anti-CD 56, more preferably anti CD 138, and anti-CD 38, even more preferably anti CD-138. Such ligands may be conjugated to colloidal magnetic particles by methods that are substantially similar to the methods disclosed U.S. Pat. No. 6,365,662. Two or more ligands may be used in step (b) of the invention and it is preferred that at least two ligands are used in that step.

The term "magnetic field" may be produced by any of a number of methods, particularly by two magnetic separators substantially as described in U.S. Pat. No. 7,901,950, which is incorporated by reference in its entirety. The term "additional marker" means a cell associated protein that is specific for CMMC or excludes CMMCs. Such proteins include but are not limited to antibodies selected from the group consisting of anti-CD38 anti CD19, and anti CD45 anti CD 138, anti CD 56, anti lambda, anti kappa anti CD 200, anti Ki67. Such antibodies may be labeled with indicators such as phycoertythrin, fluorescein isothiocyanate, and allophycocyanin and it is preferable that they are labeled with one or more markers. Additional marker may include nucleic acid dyes such as DAPI. The preferred additional marker is selected from the group consisting of anti-CD38, anti CD19, and anti CD45; the particularly preferred additional marked is anti CD38. Two or more additional markers may be used in step (d) of the invention and it is preferred that at least two additional markers are used, more preferably, three additional markers, most preferably four additional markers.

The term "analyzing" means evaluating the magnetically captured sample to determine one or more of the following: whether the sample contains CMMCs or CPCs. Such identification may be conducted by visually or electronically to determine the degree of fluorescence of a magnetically captured samples. Such analysis methods are disclosed in U.S. Pat. No. 7,011,794 which is hereby incorporated by reference. Particularly, magnetically captured samples that are positive for CD38 and negative for CD19 and CD45 are identified as CMMCs.

The invention includes a method of determining if a patient's is likely candidates for therapeutic intervention for diseases associated with abnormal plasma cells (a) processing said patient's blood to determine how many CMMC are in sample (b) determining by counting if the number of CMMC cells present in said sample, is equal to or greater than or equal to the normal range As used herein the terms sample has its aforementioned meaning and preferred range. The term "processing" means treating a sample of patient's blood by the methods described herein to isolate and identify CMMCs.

The term "therapeutic intervention" seeking or obtaining any medical intervention for treating diseases associated with abnormal plasma levels. Such diseases include but are not limited to Multiply Myeloma, MGUS, and Smoldering Multiple Myeloma. Such therapeutic intervention includes but is not limited to visiting a physician, obtaining therapeutic treatment such as radiation, and treatment with of drugs that treat any of the diseases associated with abnormal plasma levels, and monitoring the effect of such therapeutic treatments. For example, if a patient is being treated with a drug, the patient's levels of CMMC may be assessed during the course of treatment to determine if the drug is working. Such drugs include but are not limited to, Dexamethasone, cyclophosphamide, Vincristine, Bortezomib, Melphalan, Zometa, Aloxi, Lenalidomide, Doxirubicin, and the like.

The term "normal range" means the number of CMMC cells present in a sample population that does not have diseases associated with abnormal plasma cells. Preferably the normal range is less than 7 CMMCs in a blood sample of about 3 mL to about 7.5 mL. The term "greater than the normal range" is a number of CMMCs in excess of the normal range. The higher this number, the more likely it is that the patient either has one of the diseases associated with abnormal plasma cells. If a patient has between 8 and 20 CMMCs in a sample of blood such patient has a higher probability of having one of the diseases associated with abnormal plasma cells. If a patient has between 21 and 49 CMMCs the patient has an elevated level and is more likely to have one of the diseases associated with abnormal plasma cells, if a patient has between 50 and tens of thousands of CMMCs that patient has a highly elevated level and even more likely to have one of such diseases.

Yet still further, the invention includes a method of determining whether a patient undergoing therapeutic intervention is reducing the number of CMMCs comprising
(a) processing said patient's blood to determine how many CMMC are in sample at a first point in time
(b) determining by counting if the number of CMMCs present in said sample, is equal to or greater than or equal to the normal range
(c) processing said patient's blood to determine how many CMMC are in sample at a second point in time
(d) determining by counting if the number of CMMCs present in said sample, is equal to or greater than or equal to the normal range
(e) comparing the numbers in steps (b) and (d).

All of the afore-defined terms have their same meaning and preferred range.

Still further, the invention includes a method of determining whether a patient who had a disease of abnormal plasma cells and has been successfully treated for such disease, remains in remission comprising
(a) processing said patient's blood to determine how many CMMC are in sample at a first point in time
(b) determining by counting if the number of CMMCs present in said sample, is equal to or greater than or equal to the normal range
(c) processing said patient's blood to determine how many CMMC are in sample at a second point in time
(d) determining by counting if the number of CMMCs present in said sample, is equal to or greater than or equal to the normal range
(e) comparing the numbers in steps (b) and (d).

All of the afore-defined terms have their same meaning and preferred ranges.

Still even further the invention includes a reagent for capturing circulating multiple myeloma cells comprising colloidal magnetic particles and at least one ligand.

All of the afore-defined terms have their same meaning and preferred ranges.

Yet still further, the invention includes methods of capturing isolating, and analyzing circulating plasma cells comprising
(a) obtaining a sample of blood from a test subject
(b) contacting said sample with colloidal magnetic particles that are conjugated to a first ligand
(c) subjecting the sample of step (b) to a magnetic field to produce a separated fraction of magnetic particle-bound circulating multiple myeloma cells
(d) treating the sample of step (c) with a first additional marker
(e) analyzing circulating plasma cells.

All of the afore-defined terms have their same meaning and preferred ranges.

Circulating Multiple Myeloma Cells (CMMC), a form of abnormal plasma cells, captured from blood have been captured and analyzed using the CellTracks® AutoPrep® and CellTracks Analyzer II® System. In this procedure, a combination of capture reagent (ferrofluid) and fluorescent biomarkers (such as anti-CD38-Phycoerythrin (PE) antibody) and dyes (such as the nucleic acid dye DAPI) are used to identify abnormal plasma cells and to distinguish them from contaminating leukocytes and debris. CD138 or Syndecan-1 is a cell surface marker found on mature plasma cells and on plasma cell malignancies such as multiple myeloma but not on other normal peripheral blood leukocytes. For this reason anti-CD138 was coupled to ferrofluid, magnetic nanoparticles, which are used to magnetically select circulating plasma cells from a sample of peripheral blood. In order to detect the abnormal plasma cells from contaminating leukocytes several fluorescent biomarkers are used. Anti-CD38 is conjugated to phycoerythrin (PE) and is used as a positive marker for the detection of plasma cells. However since CD38 is also found on some types of leukocytes (activated T and B cells) the assay also uses allophycocyanine (APC) conjugated anti-CD45 and anti-CD19 conjugated to allophycocyanin (APC) as a negative marker. CD45 is a pan-leukocyte marker found on peripheral blood leukocytes and CD19 is a specific B cell marker. Myeloma cells are functionally differentiated B cells which do not express either CD45 or CD19. A final marker in this assay is anti-CD56 conjugated to fluorescein isothiocyanate (FITC). CD56 can be found on some peripheral leukocyte subsets such as NK cells but is also expressed on 75% of myeloma cells and is often associated with poorer patient prognosis. So while CD56 is neither a positive or negative marker for multiple myeloma its expression levels on cells can be monitored during patient drug therapy.

The assay was initially developed using cell lines such as RPMI 8226, H929 and MM.1S to evaluate different antibodies to the markers determined to be present on Multiple Myeloma cells which include CD138, CD38 and CD56. Since these cells lines were negative for CD45 and CD19, PBMC were used instead to evaluate those antibodies.

The enriched and stained cells were transferred to a CellTracks® cartridge and MagNest® for magnetic mounting. The cartridge was scanned using the CellTracks Analyzer II®. Individual images of cells were presented to the operator for review, and scored as CMMCs, based on fluorescence and cell morphology. In a model spike-in system the assay consistently recovered ~60% of the cells from the Multiple Myeloma cell line H929 spiked into 4.0 mL of blood from healthy donors. The assay was linear over the tested range of from 0 to 2000 spiked H929 cells (r2 0.98, slope 0.50, intercept 10). The assay was validated using blood from age matched healthy donors (n=22) and patients with Multiple Myeloma (n=66) and MGUS (n=7). In 4.0 mL blood from normal donors, 0 CPC were detected in 12/22 (55%) and low numbers (1-6 CPC) were detected in 10/22 (45%) samples. Interestingly, one CD56 positive CPC was found in a normal donor. CMMC in Multiple Myeloma patients ranged from 0-17,000/4.0 mL blood. One or more CMMC were detected in 91% of the patients, ≥5 in 68%, ≥10 in 58% and ≥100 in 35%. Expression of CD56 was highly variable in the patient population. CMMC in MGUS patients ranged from 0-112/4.0 mL blood. One or more CMMC were detected in 6/7 of the patients, >5 in 4/6, >10 in 2/6 and >100 in 1/6.

To further characterize CMMC, and differentiate CPC from CMMC, an interphase fluorescent in situ hybridization (FISH) assay was developed to be used with the capture and detection system described above. A four color FISH probe was used to simultaneously detect high risk mutations. The following examples illustrate the invention

EXAMPLES

Abbreviations

PE—Phycoerythrin
FITC—Fluorescein isothiocyanate
APC—Allophycocyanin

PBMC—peripheral blood mononuclear cell

Antibody Sources—

CD138:
Gen-Probe Diaclone SAS
1 Bd A Fleming, BP 1985
F-25020 Besancon Cedex, France
CD38 and CD19
R&D Systems
614 McKinley Place N.E.
Minneapolis, Minn. 55413

Example 1

Capture Targets

Figure 1:
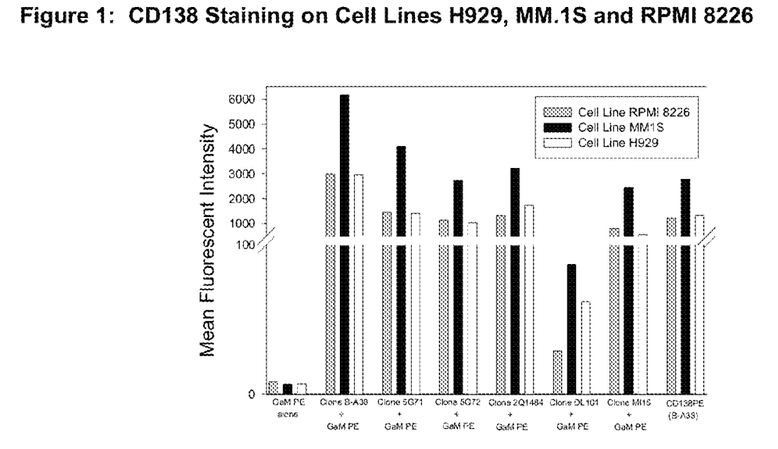
FIG. 1 illustrates the reactivity of CD 138 antibodies with certain cell lines

FIG. 1 shows that of the anti-CD138 antibodies tested for reactivity with the cell lines RPMI 8226, H929, and MM.1S, the best performing antibody was clone B-A38. The cell lines were first labeled with the different antibodies, which were all mouse anti-human antibodies, then subsequently labeled with an anti-mouse PE conjugate and analyzed by flow cytometry. Clone B-A38 gave the highest fluorescent staining on all the Multiple Myeloma cell lines.

Example 2

Detection Targets

Figure 2:
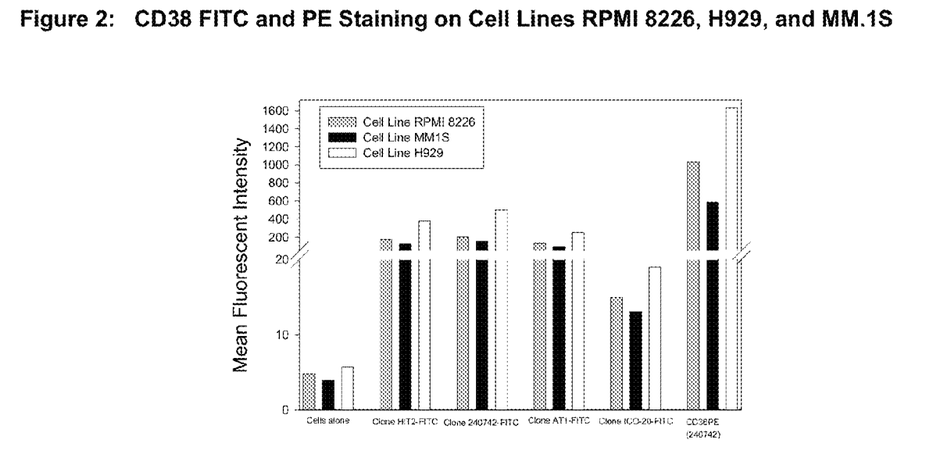
FIG. 2 illustrates the reactivity of CD 38 antibodies with certain cell lines

FIG. 2 shows that of the anti-CD38 antibodies tested for reactivity with the cell lines RPMI 8226, H929, and MM.1S the best performing antibody was clone 240742. The cell lines were initially tested using a direct anti-CD38-FITC conjugate but the FITC conjugate was later found to be not sufficiently suitable for detection on the CellTracks® platform. A PE conjugate of this antibody was subsequently prepared and tested and found to be suitable for detection.

Example 3

Dilution Determination

Figure 3:
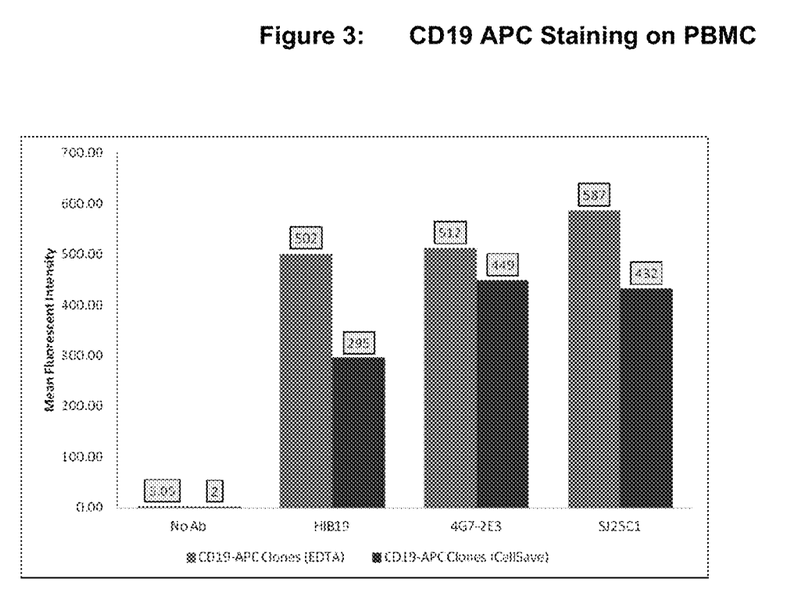
FIG. 3 illustrates the reactivity of different CD19 APC antibodies testing on PBMC
Figure 4:
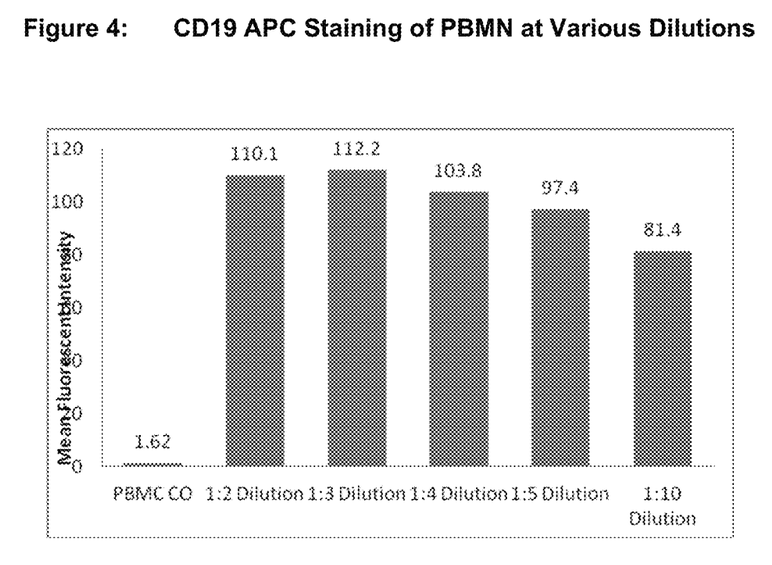
FIG. 4 illustrates staining of CD 19 APC at various dilutions

Anti CD19 and anti-CD45, both as APC conjugates, were chosen as negative detection markers as the absence of both is indicative of abnormal plasma cells. Anti-CD45APC is already a component of the CellSearch® CTC staining reagent so no further optimization was necessary. And since none of the myeloma cell lines under evaluation expressed CD19, PBMC were used to evaluate the different anti-CD19APC clones. Results of anti-CD19 testing on PBMC can be seen in FIG. 3. Staining was conducted according to the manufacturer's recommended protocols on PBMC collected from EDTA and CellSave tubes. Clone SJ25C1 was chosen as the best performing conjugate. The conjugate was then tested at various dilutions in the same reaction volumes used on AutoPrep®, FIG. 4. A dilution of 1:5 was chosen as the final dilution for staining.

Example 4

Staining CD56 and PBMC

Figure 5:
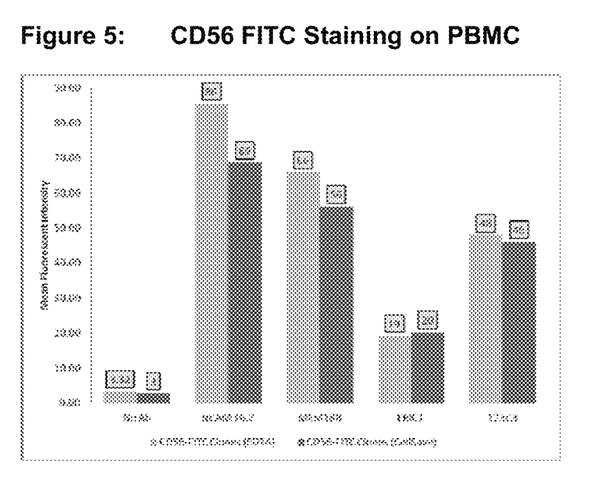
FIG. 5 illustrates staining of CD 56 antibodies on PBMC
Figure 6:
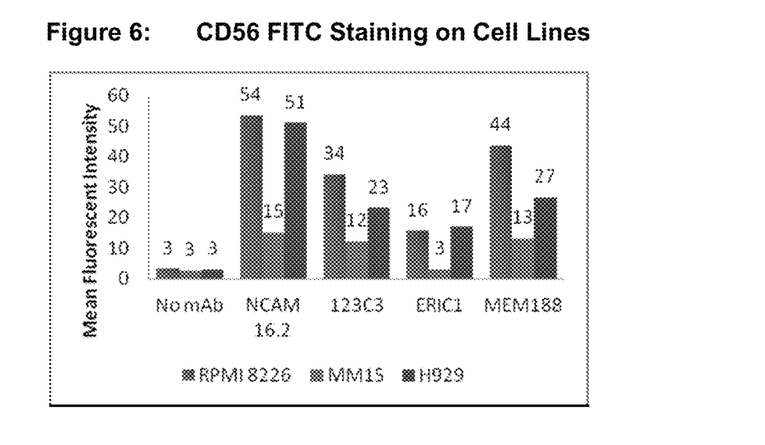
FIG. 6 illustrates staining of CD 56 staining on various cell lines.
Figure 7:
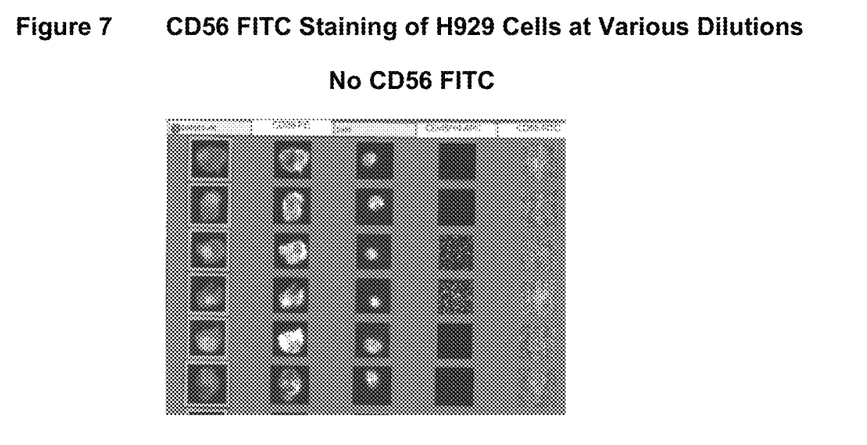
FIG. 7 illustrates staining without CD56
Figure 8:
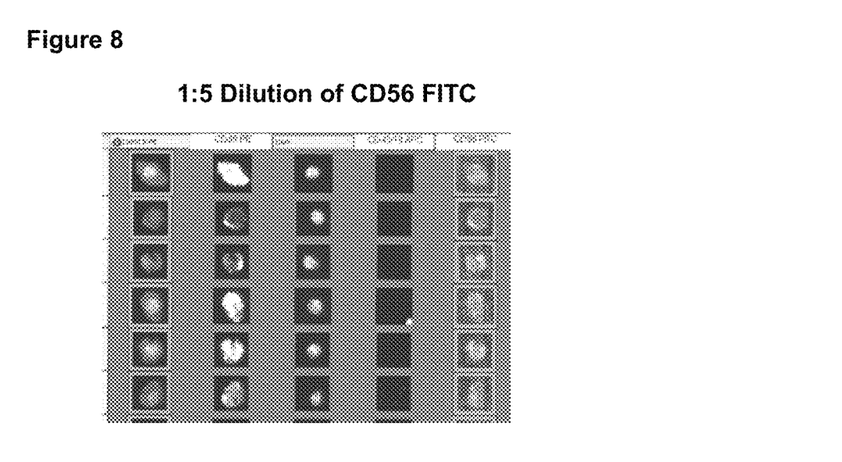
FIG. 8 illustrates CD 56 FITC staining of a cell line at a dilution
Figure 9:
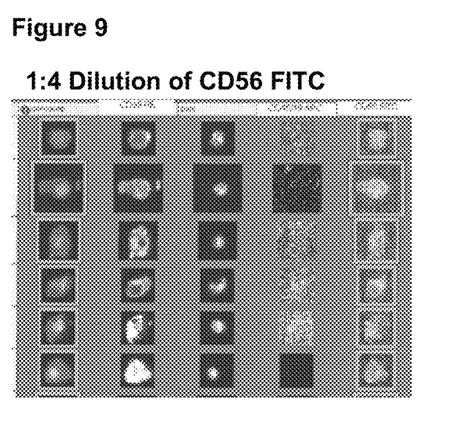
FIG. 9 illustrates CD 56 FITC staining of a cell line at a dilution

Anti-CD56 was chosen as a FITC marker reagent as it is expressed on 75% of myeloma cases with abnormal expression. Testing was conducted on cell lines (FIG. 6) and PBMC (FIG. 5) according to the manufacturer's recommended protocol. NCAM 16.2 was chosen as the best performing conjugate.

Example 5

CD 56 FITC Dilutions

The anti-CD56 FITC conjugate NCAM 16.2 was tested at various dilutions with H929 cells on AutoPrep®, see FIG. 7-10. No clear dilution tested was best on the cell line. A dilution of 1:4 was chosen as the final dilution for staining until patient samples could be tested to help determine the optimum concentration.

Example 6

Images

A CMMC prototype kit was then constructed consisting of anti-CD138 ferrofluid, staining reagent consisting of anti-CD38 PE, anti-CD45 APC and anti-CD19 APC, and an anti-CD56 FITC marker reagent. The remaining components of the kit were Capture Enhancement Reagent (PN 7037), Permeabilization Reagent (PN 7038), Nucleic Acid Dye (PN 7041), and CellFix (PN 7042). The first round of testing used anti-CD138 ferrofluid at different concentrations. The final anti-CD38 PE concentration was set at 1 µg/ml (staining reagent concentration of 5.7 µg/ml) based on the previous flow data. Final anti-CD45 APC concentration was approximately 2 µg/ml (staining reagent concentration of 13 µg/ml—same as in the CellSearch® CTC Kit) and the stock anti-CD19 APC conjugate was diluted 1:5 in the staining reagent. Anti-CD56 FITC was used at a concentration of 1:4 in the marker reagent vial. H929 cells were spiked into 7.5 mls of CellSave blood and processed on AutoPrep® at ferrofluid concentrations of 135, 185, 220, and 270 µg/ml. Samples were then analyzed on the CellTracks Analyzer II® and the recovery of H929 cells reached a plateau of 55-60% at around 220 µg/ml.

It was therefore decided that the final ferrofluid concentration in the kit would be 220 µg/ml per 7.5 ml blood sample which is similar to concentrations used in many other CellSearch® kits.

Figure 11:
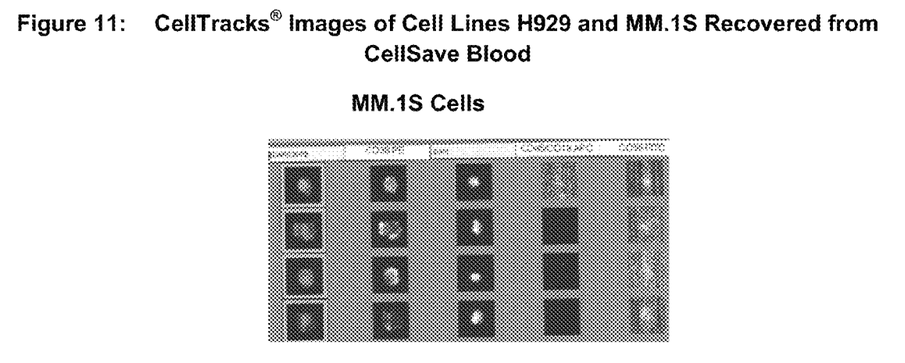
FIG. 11 illustrates representative images from MM 1-S cells
Figure 12:
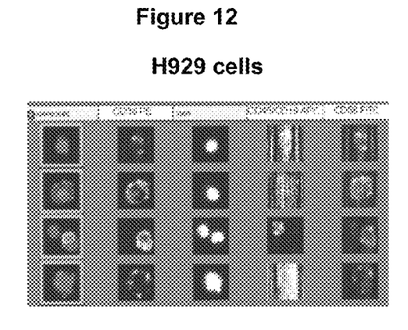
FIG. 12 illustrates representative images from H929 cells
Figure 13:
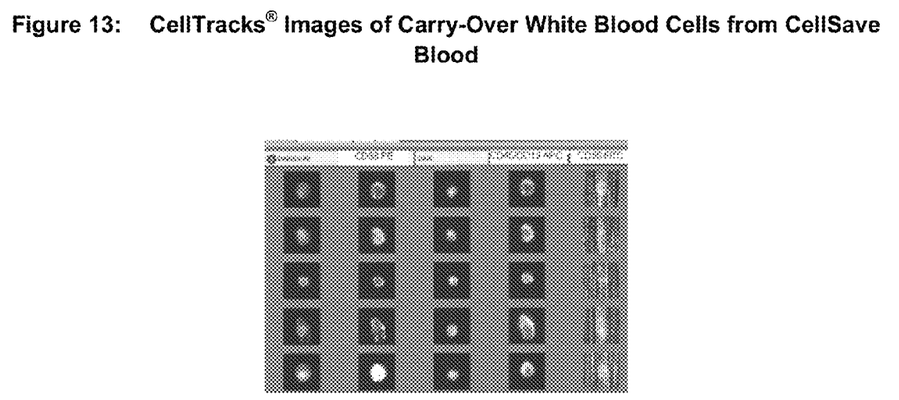
FIG. 13 illustrates representative images of carry-over white blood cells
Figure 14:
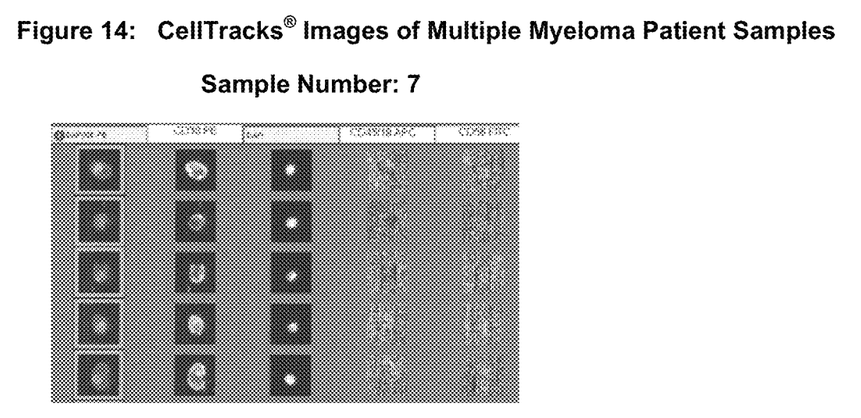
FIG. 14 illustrates images of a patient sample
Figure 15:
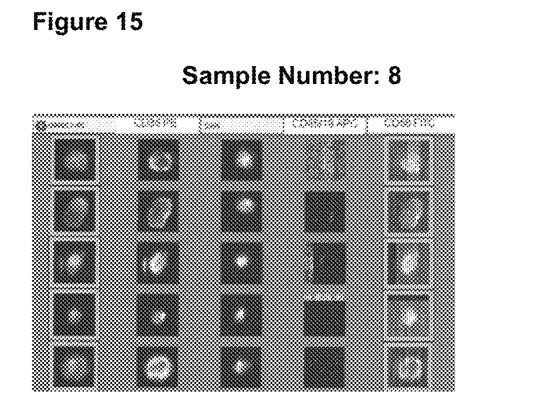
FIG. 15 illustrates images of a patient sample
Figure 16:
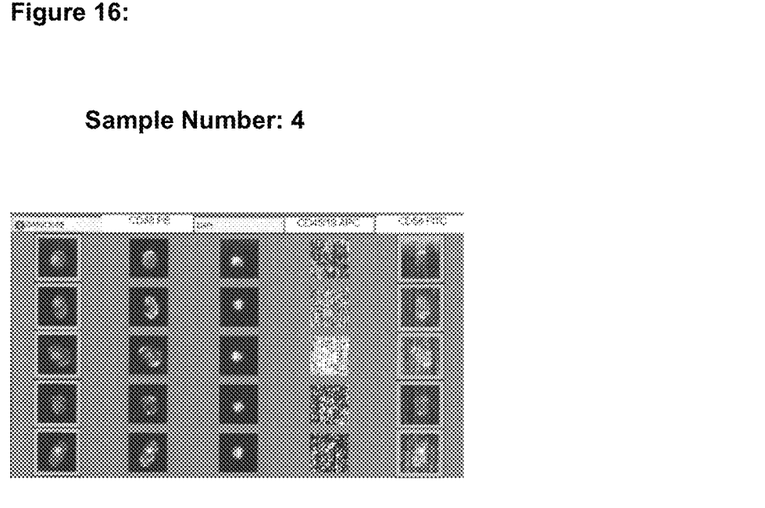
FIG. 16 illustrates images of a patient sample
Figure 17:
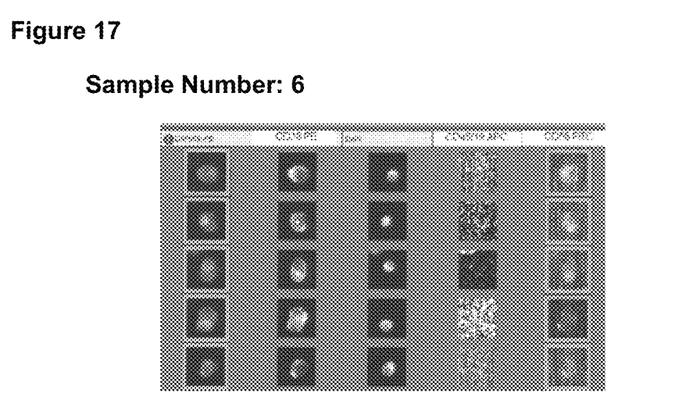
FIG. 17 illustrates images of a patient sample

CellTracks® images of recovered H929 and MM.1S cells can be seen in FIGS. 11 and 12 respectively. Note the greater CD56 staining of H929 cells compared to the MM.1S cells. Carryover white blood cells (CD38+/CD45+) can be seen in FIG. 13.

Example 7

Patient Samples

Figure 10:
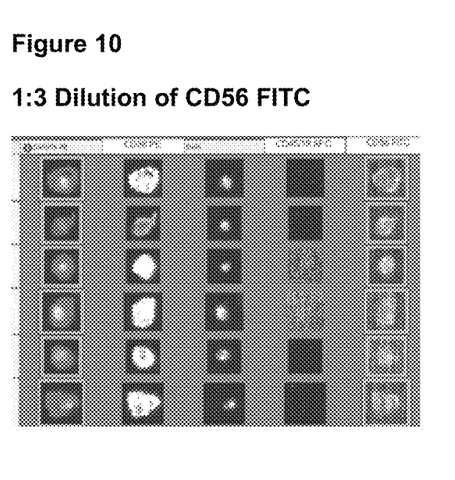
FIG. 10 illustrates CD 56 FITC staining of a cell line at a dilution

A total of 66 Multiple Myeloma patient samples were tested for CMMC. These samples were acquired from Conversant and originally 7.5 mLs of blood was tested using the CellTracks® CMMC service kit but as it became apparent that many samples had high numbers of CMMC a decision was made to reduce the volume of blood tested to 4 mLs. Samples were processed on the CellTracks® AutoPrep® and then scanned on the CellTracks Analyzer II®. FIG. 10 is a table of data generated from the patient blood samples. CMMC in Multiple Myeloma patients ranged from 0-17,000/4.0 mL blood. One or more CMMC were detected in 91% of the patients, ≥5 in 68%, ≥10 in 58% and ≥100 in 35%. Expression of CD56 was highly variable in the patient population. CMMC in MGUS patients ranged from 0-112/4.0 mL blood. One or more CMMC were detected in 6/7 of the patients, >5 in 4/6, >10 in 2/6 and >100 in 1/6. FIGS. 14-17 shows some representative CellTracks® images from patient samples.

Legend Table 1

Stage: A diagnostic classification of the extent and characteristics of myeloma cells comprising Stages I, II, and III. The number of cancers cells progresses from relatively few to moderate to relatively large as the Stages progress. Additional symptoms such as M protein, anemia, and serum calcium also increase as the Stages progress.

Treatment status: Reflects the disease status and approach to treatment

Treatment type: Drug or radiation therapy

Volume: Volume of peripheral blood processed on the CellSearch® System

Total events: Total number of CellTracks® browser images presented to the user for a manual classification of Multiple Myeloma cells Total MM Cells (CD38+, CD19/45−): Total number of images from the total events that the user has determined to meet the criteria of a Multiple Myeloma (MM) cell. These cells are CD38 positive and CD19/45 negative.

CD38+, CD19/45−, CD56+: The number of Multiple Myeloma cells that were CD56 positive CD38+, CD19/45—, CD56−: The number of Multiple Myeloma cells that were CD56 negative Unassigned events: The total events minus the total MM cells, which were events the user classified as Multiple Myeloma cells. Unassigned events are a combination of white blood cells, computer noise, or other debris not classified as MM cells.

TABLE 1

Table of CMMC Multiple Myeloma Patient Samples

| Sample | Gender/Age | Treatment Status | Treatment Type | Stage | Volume (mLs) | Total Events | Total MM Cells CD38+, CD45/19− | CD38+, CD45/19− CD56+ | CD38+, CD45/19− CD56− | Unassigned Events |
|---|---|---|---|---|---|---|---|---|---|---|
| 1 | M/78 | Active | Revlimid, Decadron | II | 7.5 | 5491 | 1 | 1 | 0 | 5490 |
| 2 | M/66 | Active | Velcade, Doxil, Decadron | III | 7.5 | 2118 | 4 | 3 | 1 | 2114 |
| 3 | F/78 | Refractory | Post Velcade, Doxil, Dexamethasone, Revlimid | III | 7.5 | 3179 | 16 | 15 | 1 | 3163 |
| 4 | M/61 | Active | Revlimid, Doxil | III | 7.5 | 33090 | 20681 | 19399 | 1282 | 12409 |
| 5 | M/54 | Pre | N/A | I | 7.5 | 4387 | 6 | 0 | 6 | 4381 |
| 6 | F/62 | Active | Dexamethasone, Doxil, Velcade | II | 7.5 | 6500 | 1931 | 1515 | 416 | 4569 |
| 7 | F/63 | Post | NA |  | 4 | 20383 | 16814 |  |  | 3569 |
| 8 | M/56 | Active | Decadron | II | 7.5 | 21091 | 17779 | 0 | 17779 | 3312 |
| 9 | M/57 | Active | Radiation |  | 4 | 42388 | 16447 | 0 | 16447 | 25941 |
| 10 | F/67 | Active | Velcade | I | 7.5 | 3879 | 11 | 10 | 1 | 3868 |
| 11 | M/48 | Active | Velcade, Decadron, Doxil | III | 7.5 | 8664 | 2 | 1 | 1 | 8662 |
| 12 | F/53 | Active | Velcade | II | 7.5 | 1102 | 3 | 2 | 1 | 1099 |
| 13 | F/77 | Active | Velcade, Dexamethasone | I | 4 | 5104 | 23 | 8 | 15 | 5081 |
| 14 | M/79 | Active | Revalmid, Dexamethasone | III | 4 | 2893 | 0 | 0 | 0 | 2893 |
| 15 | F/68 | Active | Cytoxan | III | 4 | 960 | 3 | 0 | 3 | 957 |
| 16 | F/40 | Active | Velcade | II | 4 | 6937 | 5092 | 2213 | 2879 | 1845 |
| 17 | F/41 | Post | NA |  | 4 | 760 | 0 |  |  | 760 |
| 18 | M/76 | Active | Velcade | II | 4 | 1818 | 6 | 4 | 2 | 1812 |
| 19 | M/53 | Active | Dexamethasone | I | 4 | 6966 | 3 | 0 | 3 | 6963 |
| 20 | F/76 | Active | Velcade | III | 4 | 1630 | 26 | 4 | 22 | 1604 |
| 21 | F/79 | Recurrent | NA | III | 4 | 12834 | 5428 | 2451 | 2977 | 7406 |
| 22 | F/80 | Post | In between |  | 4 | 9472 | 4 | 1 | 3 | 9468 |
| 23 | F/80 | Pre | NA |  | 4 | 2408 | 145 |  |  | 2263 |
| 24 | F/80 | Pre | NA |  | 4 | 1197 | 249 |  |  | 948 |
| 25 | M/79 | Active | Velcade | II | 4 | 6792 | 788 | 68 | 720 | 6004 |
| 26 | M/79 | Active | Aloxi, Doxil, Vincristin |  | 4 | 17128 | 103 | 18 | 85 | 17025 |
| 27 | M/73 | Post | NA |  | 4 | 552 | 48 | 34 | 14 | 504 |
| 28 | M/74 | Post | NA |  | 4 | 584 | 22 | 5 | 17 | 562 |
| 29 | M/74 | Post | NA |  | 4 | 5293 | 13 |  |  | 5280 |
| 30 | M/59 | Active | Velcade, Doxil |  | 4 | 2302 | 3 | 1 | 2 | 2299 |
| 31 | F/60 | Post | NA |  | 4 | 1237 | 148 | 110 | 38 | 1089 |
| 32 | F/60 | Post | NA |  | 4 | 4436 | 89 | 81 | 8 | 4347 |
| 33 | F/61 | Between | NA |  | 4 | 1804 | 27 |  |  | 1778 |
| 34 | F/61 | Pre | NA |  | 4 | 3941 | 99 | 27 | 72 | 3842 |
| 35 | F/61 | Active | Velcade |  | 4 | 2126 | 14 |  |  | 2112 |

TABLE 1-continued

Table of CMMC Multiple Myeloma Patient Samples

| Sample | Gender/Age | Treatment Status | Treatment Type | Stage | Volume (mLs) | Total Events | Total MM Cells CD38+, CD45/19− | CD38+, CD45/19− CD56+ | CD38+, CD45/19− CD56− | Unassigned Events |
|---|---|---|---|---|---|---|---|---|---|---|
| 36 | F/61 | Active | Bortezomib | | 4 | 1289 | 7 | | | 1282 |
| 37 | M/69 | Active | Revlimid | | 4 | 934 | 38 | 26 | 12 | 896 |
| 38 | F/69 | Active | Cytoxan | | 4 | 890 | 12 | 0 | 12 | 878 |
| 39 | F/72 | Active | Doxil, Velcade | | 4 | 669 | 0 | 0 | 0 | 669 |
| 40 | F/59 | Active | Doxil, Velcade | | 4 | 4921 | 335 | 100 | 235 | 4586 |
| 41 | F/59 | Active | Doxil, Velcade | | 4 | 3098 | 221 | 37 | 184 | 2877 |
| 42 | F/60 | Active | Velcade | | 4 | 272 | 0 | 0 | 0 | 272 |
| 43 | F/60 | Active | Bortezomib | | 4 | 277 | 1 | | | 276 |
| 44 | F/61 | Active | Doxil, Velcade | | 4 | 2511 | 253 | 171 | 82 | 2258 |
| 45 | F/61 | Active | Doxil, Velcade | | 4 | 933 | 215 | 46 | 169 | 718 |
| 46 | F/61 | Pre | NA | | 4 | 2264 | 95 | | | 2169 |
| 47 | M/70 | Active | Doxil, Melphalan | | 4 | 1300 | 0 | 0 | 0 | 1300 |
| 48 | M/75 | Active | Velcade | | 4 | 4658 | 2 | 0 | 2 | 4656 |
| 49 | M/63 | Post | NA | | 4 | 14448 | 1 | 0 | 1 | 14447 |
| 50 | M/76 | Post | Zometa | | 4 | 25095 | 2 | 1 | 1 | 25093 |
| 51 | F/68 | Post | Zometa | | 4 | 5099 | 5 | 0 | 5 | 5094 |
| 52 | M/71 | Active | Aloxi, Doxil, Vincristin | | 4 | 18684 | 49 | 9 | 40 | 18635 |
| 53 | F/45 | Active | Decadron and Revlimid | | 4 | 3285 | 0 | 0 | 0 | 3285 |
| 54 | M/78 | Post | NA | | 4 | 2182 | 16 | 0 | 16 | 2166 |
| 55 | F/62 | Active | Velcade | | 4 | 1481 | 15 | 11 | 4 | 1466 |
| 56 | F/63 | Pre | NA | | 4 | 5681 | 581 | | | 5100 |
| 57 | F/63 | Pre | NA | | 4 | 1530 | 389 | | | 1141 |
| 58 | M/75 | Pre | NA | | 4 | 14232 | 199 | 4 | 195 | 14033 |
| 59 | F/63 | Post | NA | | 4 | 9610 | 1 | 0 | 1 | 9609 |
| 60 | M/79 | Active | Radiation | | 4 | 4121 | 4121 | 0 | 4121 | 0 |
| 61 | M/62 | Post | NA | | 4 | 1494 | 8 | | | 1486 |
| 62 | F/59 | Active | Bortezomib | | 4 | 1956 | 398 | | | 1558 |
| 63 | M/50 | Active | Lenalidomide | | 4 | 1276 | 7 | | | 1269 |
| 64 | M/62 | Active | Doxirubicin | | 4 | 9470 | 1842 | | | 7628 |
| 65 | M/60 | Post | NA | | 4 | 1055 | 2 | 0 | 2 | 1053 |
| 66 | M/53 | Active | Bortezomib | | 4 | 813 | 376 | 131 | 244 | 437 |

Example 8

Normal Subjects

Figure 18:
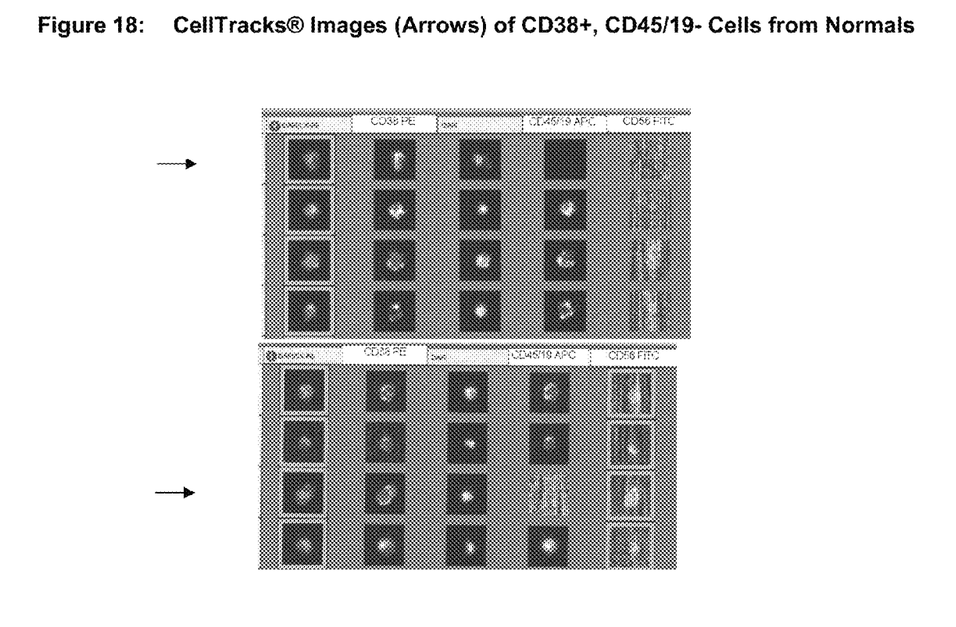
FIG. 18 illustrates images from normal donors

Twenty two age-matched normals were then tested as well. These samples were also acquired from Conversant and 4 mls of blood was tested using the CellTracks® CMMC service kit. Samples were processed on the CellTracks® AutoPrep® and then scanned on the CellTracks Analyzer II®. Table 2 is a table of data generated from the 4 ml blood samples. In 4.0 mL blood from normal donors, 0 CPC were detected in 12/22 (55%) and low numbers (1-6 CPC) were detected in 10/22 (45%) samples. Interestingly, one CD56 positive CPC was found in a normal donor. See FIG. 18. The average number of total browser events was approximately 1500.

To further characterize CMMC, and differentiate CPC from CMMC, an interphase fluorescent in situ hybridization (FISH) assay was developed to be used with the capture and detection system described above. A four color FISH probe was used to simultaneously detect high risk mutations including two recurrent translocations of the IgH locus (t(4;14)(p16;q32) and t(14;16)(q32;q23)) as well as deletion of the TP53 locus (Δ17p13). The FISH assay was verified on cell lines H929, MM1s, and U266, which showed mutations at t(4;14), t(14;16) and Δ17p13, respectively. The FISH assay was tested on 9 CMMC patient samples and 8 samples yielded evaluable results. Two samples showed t(4;14) fusions, 3 patients showed aberrant FISH signal patterns indicating aneuploidy of chromosome 4 or 14 and the remaining patients showed normal FISH patterns.

TABLE 2

Table of CMMC from 4 mls Age-Matched Normal Blood Donors

| Sample | Gender/Age | Volume (mLs) | Total Events | CD38+, CD45/19− CD56+ | CD38+, CD45/19− CD56− | Unassigned Events |
|---|---|---|---|---|---|---|
| 1 | F/43 | 4 | 3281 | 0 | 1 | 2538 |
| 2 | M/71 | 4 | 1939 | 0 | 0 | 759 |
| 3 | F/54 | 4 | 3584 | 0 | 1 | 2794 |
| 4 | F/61 | 4 | 399 | 0 | 0 | 102 |
| 5 | F/70 | 4 | 645 | 0 | 0 | 114 |
| 6 | F/60 | 4 | 526 | 0 | 0 | 273 |
| 7 | F/49 | 4 | 273 | 0 | 0 | 80 |
| 8 | F/55 | 4 | 2502 | 1 | 2 | 1559 |
| 9 | M/47 | 4 | 811 | 0 | 1 | 209 |
| 1 | F/55 | 4 | 1512 | 0 | 2 | 940 |

TABLE 2-continued

Table of CMMC from 4 mls Age-Matched Normal Blood Donors

| Sample | Gender/Age | Volume (mLs) | Total Events | CD38+, CD45/19-CD56+ | CD38+, CD45/19-CD56- | Unassigned Events |
|---|---|---|---|---|---|---|
| 11 | M/42 | 4 | 1032 | 0 | 0 | 485 |
| 12 | F/54 | 4 | 576 | 0 | 0 | 287 |
| 13 | M/44 | 4 | 6211 | 0 | 1 | 4742 |
| 14 | F/55 | 4 | 1891 | 0 | 0 | 1182 |
| 15 | M/43 | 4 | 1233 | 0 | 0 | 745 |
| 16 | M/50 | 4 | 816 | 0 | 0 | 524 |
| 17 | F/50 | 4 | 661 | 0 | 1 | 362 |
| 18 | F/55 | 4 | 668 | 0 | 1 | 367 |
| 19 | M/60 | 4 | 1621 | 0 | 0 | 696 |
| 20 | F/58 | 4 | 414 | 0 | 0 | 249 |
| 21 | F/60 | 4 | 2221 | 0 | 1 | 2220 |
| 22 | M/51 | 4 | 762 | 0 | 6 | 756 |

Example 9

Capture Using Anti-CD 38 and Anti CD 138 Patient Samples

Anti CD138, the cell surface marker conjugated to colloidal magnetic particles used to capture myeloma cells in the present invention can be shed from the myeloma cell surface over time. CD38, a surface marker also present on myeloma cells, does not undergo shedding from the cell surface. A magnetic nanoparticle was developed that was coupled to both anti-CD138 and anti-CD38 and tested with both patient samples and normal donors for the ability to capture myeloma cells. Anti-CD38 and anti CD 138 both conjugated to phycoerythrin (PE), and both recognizing a different epitopes than the anti CD38 and anti-CD 138 used in making the magnetic nanoparticle, was used for detection along with anti-CD45 and anti-CD19 conjugated to allophycocyanin (APC).

A total of 22 Multiple Myeloma patient samples were tested for CMMC using the alternate capture reagent. These samples were acquired from Conversant and 4 mls were processed on the CellTracks® AutoPrep® and then scanned on the CellTracks Analyzer II®. Table 3 is a table generated from the patient samples. CMMC in Multiple Myeloma patients ranged from 0-2244/4.0 mL blood. One or more CMMC were detected in 82% of patients, ≥5 in 64%, ≥10 in 59%, and ≥100 in 23%.

TABLE 3 of CMMC from Multiple Myeloma Patients

| Sample | Total Events | CD38+, CD 138+ CD19/45- Cells | Unassigned Events |
|---|---|---|---|
| 1 | 19065 | 737 | 18328 |
| 2 | 5420 | 433 | 4987 |
| 3 | 6098 | 12 | 6086 |
| 4 | 7680 | 22 | 7658 |
| 5 | 26561 | 2244 | 24317 |
| 6 | 7682 | 52 | 7630 |
| 7 | 18621 | 63 | 18558 |
| 8 | 14889 | 111 | 14778 |
| 9 | 7039 | 13 | 7026 |
| 10 | 12608 | 15 | 12593 |
| 11 | 9708 | 2 | 9706 |
| 12 | 34273 | 5 | 34268 |
| 13 | 21771 | 182 | 21589 |
| 14 | 7097 | 0 | 7097 |
| 15 | 2988 | 3 | 2985 |
| 16 | 7936 | 1 | 7935 |
| 17 | 10879 | 69 | 10810 |
| 18 | 4990 | 0 | 4990 |
| 19 | 6153 | 12 | 6141 |
| 20 | 4248 | 0 | 4248 |
| 21 | 13757 | 0 | 13757 |
| 22 | 3334 | 1 | 3333 |

Example 9

Capture Using Anti-CD 38 and Anti CD 138 Normal Samples

Twelve normal donors were then tested as well, using the same kit configuration as Example 8. These samples were in house donors and 4 mLs of blood was processed on the CellTracks® AutoPrep® and then scanned on the CellTracks Analyzer II®. Table 4 is a table generated from the 4 mL blood samples. In 4.0 mL blood from normal donors, 0 CPC were detected in 5/12 (42%) and low numbers (1-3 CPC) were detected in 7/12 (58%) of samples.

TABLE 4 of CPC from Normal Donors

| Sample | Total Events | CD38+ CD 138+, CD19/45- Cells | Unassigned Events |
|---|---|---|---|
| 1 | 7120 | 2 | 7118 |
| 2 | 13075 | 3 | 13072 |
| 3 | 9208 | 3 | 9205 |
| 4 | 29057 | 3 | 29054 |
| 5 | 20525 | 1 | 20526 |
| 6 | 19619 | 2 | 19617 |
| 7 | 6004 | 1 | 6003 |
| 8 | 14456 | 0 | 14456 |
| 9 | 8528 | 0 | 8528 |
| 10 | 7966 | 0 | 7966 |
| 11 | 17311 | 0 | 17311 |
| 12 | 5924 | 0 | 5924 |

What is claimed is:

1. A reagent for capturing circulating multiple myeloma cells comprising colloidal magnetic particles and at least two ligands, wherein the ligands are selected from the group consisting of anti CD 138, anti-CD 38, and anti-CD56.

2. The reagent of claim 1 further comprising at least three ligands.

* * * * *